US 8,074,389 B2

(12) United States Patent
Greer et al.

(10) Patent No.: US 8,074,389 B2
(45) Date of Patent: Dec. 13, 2011

(54) WRISTBAND WITH SEPARATED IMAGING AREA AND CINCH SLOT

(75) Inventors: Mark Greer, O'Fallon, MO (US); Sanjay K. Jain, Saint Louis, MO (US)

(73) Assignee: Laser Band, LLC, St. Louis, MO (US)

( * ) Notice: Subject to any disclaimer, the term of this patent is extended or adjusted under 35 U.S.C. 154(b) by 0 days.

(21) Appl. No.: 12/435,541

(22) Filed: May 5, 2009

(65) Prior Publication Data
US 2010/0281724 A1    Nov. 11, 2010

(51) Int. Cl.
*A44C 5/00*    (2006.01)
(52) U.S. Cl. .................. 40/633; 40/665; 283/75
(58) Field of Classification Search ............ 40/633, 40/665
See application file for complete search history.

(56) References Cited

U.S. PATENT DOCUMENTS

| | | |
|---|---|---|
| 230,455 A | 7/1880 | Wilcox |
| 0,919,983 A | 4/1909 | Walsh |
| 0,922,948 A | 5/1909 | Portmore |
| 1,383,335 A | 7/1921 | Penksa |
| 1,517,456 A | 12/1924 | Pulliam |
| 2,054,227 A | 9/1936 | Nichols |
| 2,073,280 A | 3/1937 | Lederer |
| 2,553,676 A | 5/1951 | Roos |
| 2,641,074 A | 6/1953 | Richmond |
| 2,687,978 A | 8/1954 | Vogt |
| 3,153,869 A | 10/1964 | Twentier |
| 3,197,899 A | 8/1965 | Twentie |
| 3,402,808 A | 9/1968 | Yannuzzi |
| 3,517,802 A | 6/1970 | Petrie |
| 3,585,743 A | 6/1971 | Jeffers |
| 3,660,916 A | 5/1972 | McDermott et al. |
| 3,854,229 A | 12/1974 | Morgan |
| 4,004,362 A | 1/1977 | Barbieri |
| 4,078,324 A | 3/1978 | Wiebe |
| 4,142,310 A * | 3/1979 | Groselak et al. ............... 40/665 |

(Continued)

FOREIGN PATENT DOCUMENTS

DE    202009015077 U1    1/2010
(Continued)

OTHER PUBLICATIONS

International Preliminary Report on Patenability (Chapter II) for PCT/US2009/031979 issued May 21, 2010.
International Preliminary Report on Patentability (Chapter II) for PCT/US2009/039183 issued Apr. 20, 2010.

(Continued)

*Primary Examiner* — Joanne Silbermann
*Assistant Examiner* — Kristina N Staley
(74) *Attorney, Agent, or Firm* — Thompson Coburn LLP

(57) ABSTRACT

A printer processible wristband has a cinch slot at one end and an imaging area at another, connected with a strap therebetween. The imaging area is shaped like a shovel and the cinch slot is shaped like a "D" and sized so that the imaging area interference fits through the cinch slot to thereby join the wristband about the wrist. The imaging area may have one of its ends adhered to the strap to clamp it in place and further secure the wristband or it may be left loose to act as a hang tag. Alternate embodiments are disclosed including providing a self adhering label to attach to the imaging area, providing a layer of laminate to laminate the printed information or label, providing a second imaging area along with a second strap, and providing a snap closure to further attach the wristband.

44 Claims, 14 Drawing Sheets

U.S. PATENT DOCUMENTS

| | | | |
|---|---|---|---|
| 4,179,833 A | 12/1979 | Knodel | |
| 4,226,036 A | 10/1980 | Krug | |
| 4,233,715 A | 11/1980 | McDermott | |
| 4,370,370 A | 1/1983 | Iwata et al. | |
| 4,565,731 A | 1/1986 | Komatsu et al. | |
| 4,612,718 A | 9/1986 | Golub et al. | |
| 4,627,994 A | 12/1986 | Welsch | |
| 4,630,384 A | 12/1986 | Breen | |
| 4,682,431 A | 7/1987 | Kowalchuk et al. | |
| 4,696,843 A | 9/1987 | Schmidt | |
| 4,783,917 A | 11/1988 | Smith et al. | |
| 4,829,604 A | 5/1989 | Allen et al. | |
| 4,854,610 A | 8/1989 | Kwiatek | |
| 4,855,277 A | 8/1989 | Walter | |
| 4,914,843 A | 4/1990 | DeWoskin | |
| 4,941,210 A | 7/1990 | Konucik | |
| 4,950,638 A | 8/1990 | Yuyama et al. | |
| 4,956,931 A | 9/1990 | Selke | |
| 4,978,144 A | 12/1990 | Schmidt et al. | |
| 4,991,337 A | 2/1991 | Solon | |
| RE33,616 E | 6/1991 | Welsch | |
| 5,026,084 A | 6/1991 | Pasfield | |
| 5,045,426 A | 9/1991 | Maierson et al. | |
| 5,135,789 A | 8/1992 | Schmidt | |
| 5,222,823 A | 6/1993 | Conforti | |
| 5,227,004 A | 7/1993 | Belger | |
| 5,227,209 A | 7/1993 | Garland | |
| 5,283,969 A | 2/1994 | Weiss | |
| 5,311,689 A | 5/1994 | Lindsey | |
| 5,318,326 A | 6/1994 | Garrison | |
| 5,331,140 A | 7/1994 | Stephany | |
| 5,351,993 A | 10/1994 | Wright et al. | |
| 5,370,420 A | 12/1994 | Khatib et al. | |
| 5,381,617 A | 1/1995 | Schwartztol et al. | |
| 5,383,686 A | 1/1995 | Laurash | |
| 5,395,667 A | 3/1995 | Ohno et al. | |
| 5,418,026 A | 5/1995 | Dronzek, Jr. et al. | |
| 5,427,416 A | 6/1995 | Birch et al. | |
| 5,486,021 A | 1/1996 | Laurash | |
| 5,486,436 A | 1/1996 | Lakes | |
| 5,509,693 A | 4/1996 | Kohls | |
| 5,509,694 A | 4/1996 | Laurash et al. | |
| 5,518,787 A | 5/1996 | Konkol | |
| 5,524,934 A | 6/1996 | Schwan et al. | |
| 5,547,227 A | 8/1996 | Laurash et al. | |
| 5,560,657 A | 10/1996 | Morgan | |
| 5,581,924 A | 12/1996 | Peterson | |
| 5,586,788 A | 12/1996 | Laurash | |
| 5,595,404 A | 1/1997 | Skees | |
| 5,596,202 A | 1/1997 | Arakawa | |
| 5,598,970 A | 2/1997 | Mudry et al. | |
| 5,601,222 A | 2/1997 | Haddad | |
| 5,601,313 A | 2/1997 | Konkol et al. | |
| 5,630,627 A | 5/1997 | Stewart | |
| 5,637,369 A | 6/1997 | Stewart | |
| 5,648,143 A | 7/1997 | Mehta et al. | |
| 5,653,472 A | 8/1997 | Huddleston et al. | |
| 5,662,976 A | 9/1997 | Popat et al. | |
| 5,670,015 A | 9/1997 | Finestone et al. | |
| 5,687,903 A | 11/1997 | Akridge et al. | |
| 5,765,885 A | 6/1998 | Netto et al. | |
| 5,785,354 A | 7/1998 | Haas | |
| 5,842,722 A | 12/1998 | Carlson | |
| 5,877,742 A | 3/1999 | Klink | |
| 5,933,993 A | 8/1999 | Riley | |
| 5,984,363 A | 11/1999 | Dotson et al. | |
| 6,000,160 A | 12/1999 | Riley | |
| 6,006,460 A | 12/1999 | Blackmer | |
| 6,016,618 A | 1/2000 | Attia et al. | |
| 6,053,535 A | 4/2000 | Washburn et al. | |
| 6,055,756 A | 5/2000 | Aoki | |
| 6,058,639 A | 5/2000 | Tinklenberg et al. | |
| 6,067,739 A | 5/2000 | Riley | |
| 6,071,585 A | 6/2000 | Roth | |
| 6,092,321 A | 7/2000 | Cheng et al. | |
| 6,108,876 A | 8/2000 | Hubbert | |
| 6,155,476 A | 12/2000 | Fabel | |
| 6,155,603 A | 12/2000 | Fox | |
| 6,159,570 A | 12/2000 | Ulrich et al. | |
| 6,199,730 B1 | 3/2001 | Chisolm | |
| 6,303,539 B1 | 10/2001 | Kosarew | |
| 6,331,018 B1 | 12/2001 | Roth et al. | |
| 6,343,819 B1 | 2/2002 | Shiozaki | |
| 6,361,078 B1 | 3/2002 | Chess | |
| 6,409,871 B1 | 6/2002 | Washburn et al. | |
| 6,438,881 B1 | 8/2002 | Riley | |
| 6,510,634 B1 | 1/2003 | Riley | |
| 6,517,921 B2 | 2/2003 | Ulrich et al. | |
| 6,611,962 B2 | 9/2003 | Redwood et al. | |
| 6,641,048 B1 | 11/2003 | Schintz et al. | |
| 6,685,228 B2 | 2/2004 | Riley | |
| 6,748,687 B2 | 6/2004 | Riley | |
| 6,782,648 B1 | 8/2004 | Mosher, Jr. | |
| 6,807,680 B2 | 10/2004 | Sloot | |
| 6,836,215 B1 | 12/2004 | Laurash et al. | |
| 6,844,041 B2 | 1/2005 | Squier et al. | |
| 6,863,311 B2 | 3/2005 | Riley | |
| 6,981,948 B2 | 1/2006 | Pellegrino et al. | |
| 7,017,293 B2 | 3/2006 | Riley | |
| 7,017,294 B2 | 3/2006 | Riley | |
| 7,047,682 B2 | 5/2006 | Riley | |
| 7,197,842 B2 * | 4/2007 | Ali | 40/633 |
| 7,222,448 B2 | 5/2007 | Riley | |
| 7,240,446 B2 | 7/2007 | Bekker | |
| 7,286,055 B2 | 10/2007 | Girvin et al. | |
| 7,523,576 B1 | 4/2009 | Petty | |
| 7,763,344 B2 | 7/2010 | Riley et al. | |
| 7,779,569 B2 | 8/2010 | Riley et al. | |
| 7,779,570 B2 | 8/2010 | Riley | |
| 7,784,209 B2 | 8/2010 | Greer | |
| 7,784,210 B2 | 8/2010 | Riley et al. | |
| 2002/0152928 A1 | 10/2002 | Lawandy et al. | |
| 2002/0176973 A1 | 11/2002 | Keiser | |
| 2003/0001381 A1 | 1/2003 | Riley | |
| 2003/0003249 A1 | 1/2003 | Benim et al. | |
| 2003/0011190 A1 | 1/2003 | Ryan | |
| 2004/0068906 A1 | 4/2004 | Riley | |
| 2004/0128892 A1 | 7/2004 | Valenti | |
| 2004/0244251 A1 | 12/2004 | Riley | |
| 2005/0091896 A1 | 5/2005 | Kotik et al. | |
| 2005/0108912 A1 | 5/2005 | Bekker | |
| 2005/0279001 A1 | 12/2005 | Riley | |
| 2005/0281989 A1 | 12/2005 | Finger | |
| 2006/0230661 A1 | 10/2006 | Bekker | |
| 2006/0236578 A1 | 10/2006 | Saint et al. | |
| 2006/0242875 A1 | 11/2006 | Wilson et al. | |
| 2006/0261958 A1 | 11/2006 | Klein | |
| 2007/0089342 A1 | 4/2007 | Jain et al. | |
| 2007/0120358 A1 | 5/2007 | Waggoner et al. | |
| 2007/0220796 A1 * | 9/2007 | Riley et al. | 40/633 |
| 2007/0243361 A1 | 10/2007 | Riley et al. | |
| 2007/0257113 A1 * | 11/2007 | Davis et al. | 235/462.01 |
| 2008/0098636 A1 | 5/2008 | Greer | |
| 2009/0031602 A1 | 2/2009 | Riley | |
| 2009/0094872 A1 | 4/2009 | Ali et al. | |
| 2009/0094873 A1 | 4/2009 | Riley | |
| 2009/0193701 A1 | 8/2009 | Greer | |
| 2009/0277061 A1 | 11/2009 | Jain et al. | |
| 2009/0282717 A1 | 11/2009 | Jain et al. | |
| 2010/0071241 A1 | 3/2010 | Jain et al. | |

FOREIGN PATENT DOCUMENTS

| | | |
|---|---|---|
| EP | 1039431 | 9/2000 |
| EP | 1974603 A2 | 10/2008 |
| FR | 2806594 A | 9/2001 |
| GB | 960859 | 6/1964 |
| GB | 2045718 | 11/1980 |
| GB | 2160492 | 12/1985 |
| GB | 2228915 A | 9/1990 |
| JP | 63175913 A | 11/1988 |
| JP | 5-61777 | 8/1993 |
| JP | 08-190350 | 7/1996 |
| JP | 08299035 A | 11/1996 |
| JP | 3032299 | 12/1996 |
| JP | 10-207374 | 8/1998 |
| JP | 11015383 A | 1/1999 |
| JP | 2001316921 A | 11/2001 |

| | | | |
|---|---|---|---|
| JP | 2002117190 A | 4/2002 | |
| JP | 2002351321 A | 12/2002 | |
| JP | 2003066849 | 3/2003 | |
| JP | 2003157010 | 5/2003 | |
| JP | 2003164307 | 6/2003 | |
| JP | 2006039209 | 2/2006 | |
| WO | 9502877 | 1/1995 | |
| WO | 96/12618 | 5/1996 | |
| WO | 98/23081 | 5/1998 | |
| WO | 99/18817 | 4/1999 | |
| WO | 02/39412 | 5/2002 | |
| WO | 03/003331 | 1/2003 | |
| WO | 2004/028826 | 4/2004 | |
| WO | 2005/064574 | 7/2005 | |
| WO | 2006/007356 | 1/2006 | |
| WO | 2007/021375 | 2/2007 | |
| WO | 2007/133906 | 11/2007 | |
| WO | 2008/079952 A2 | 7/2008 | |
| WO | 2009099787 A1 | 8/2009 | |
| WO | 2009/137195 | 11/2009 | |

OTHER PUBLICATIONS

International Preliminary Report on Patentability (Chapter II) for PCT/US2008/059616 dated Jul. 14, 2009.
International Search Report for PCT/US2009/039183 dated Jun. 25, 2009.
International Preliminary Report on Patentability (Chapter I) for PCT/US20081064972 dated Dec. 1, 2009.
"Yes, Sir, That's My Baby!," Material Management in Health Care, Feb. 1999, vol. 8, No. 2, Health Forum, Inc.
Avery Laminated Identification Cards #5361.
Avery Dennison DuraCard Date.
Brochure entitled: "Integrated Document Management Software"; Smead Manufacturing Company; Date Unknown; Form No. SLI-95.
Brochure entitled: "Color-Bar a Folders"; Smead Manufacturing Company; Date Unknown.
Brochure entitled: "Color-Bara—Click Stripa Labeling System"; Smead Manufacturing Company; Date Unknown; Form No. SSS-CS-00.
Catalog entitled: "Reseller Catalog Number One"; Smead Software Solutions ; Date Unknown; Form No. SSS-RC1-00.
Disaster Management Systems, Inc., Triage Tag, Copyright 1996, Pomona, California.
Gretchen Berry, "Wrist Watch," Advance for Healthcare Information Professionals, Feb. 15, 1999.
ID Warehouse (http://web.archive.org/web/20050131235601/http://idwarehouse.com/) Jan. 31, 2005. p. 1: WB1908, Stock Vinyl Wristband.
International Search Report for PCT/US2009/031979 dated Mar. 9, 2009.
Maryland Department of Transportation, Maryland Emergency Medical Services, Triage Tag, Copyright MIEMMS 1999, Maryland.
Posey Movable I.D. Bracelet; downloaded from http:/www.posey.com/products/4648.html on Aug. 18, 2004.
Sample of Standard Register Label, Jan. 26, 1999.
Sample of Standard Register Labels.
Standard Register, P.S. Magazine, Fall 1998, Dayton, Ohio.

* cited by examiner

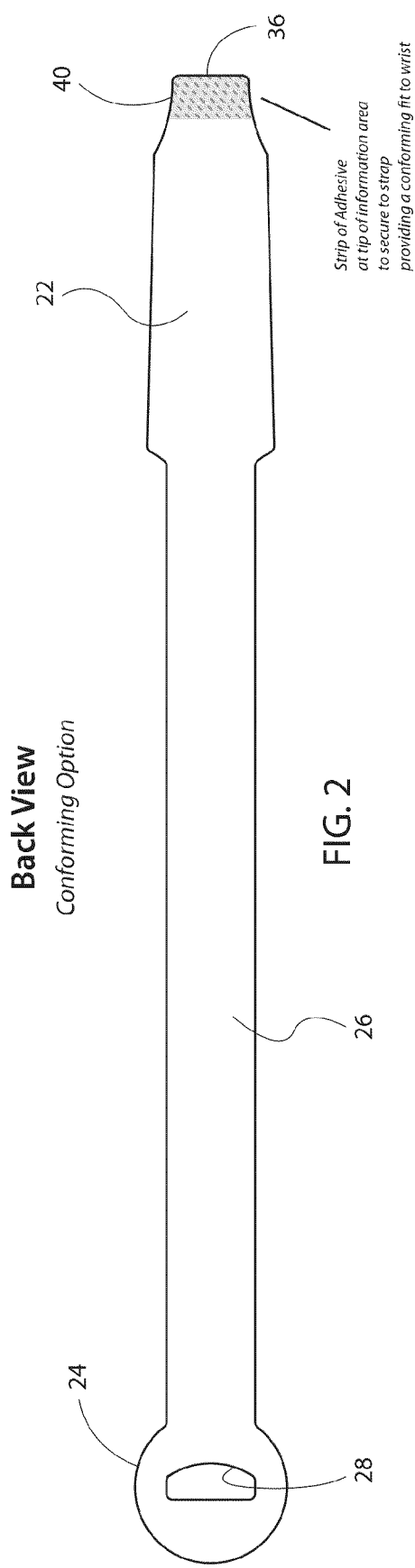
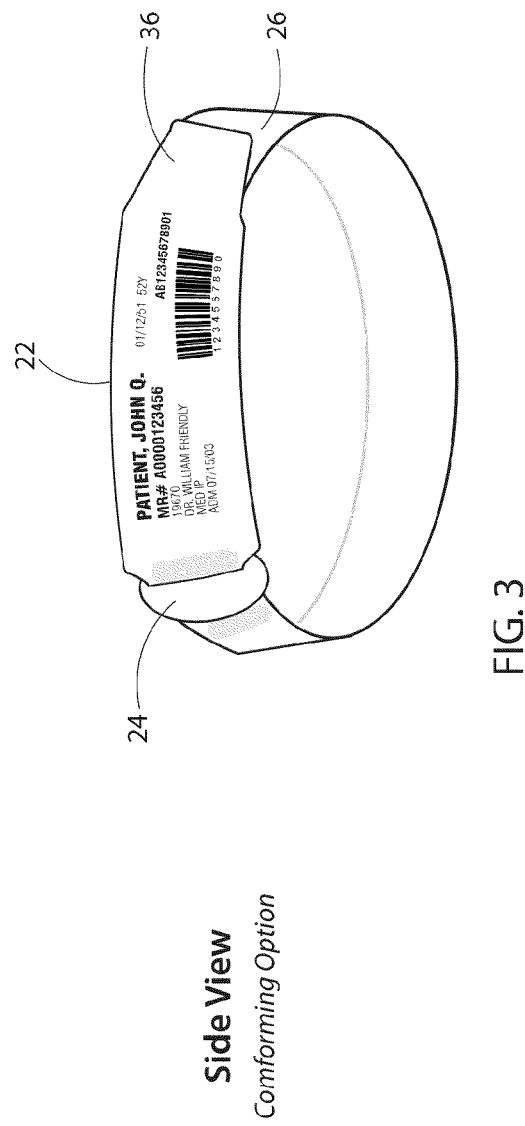

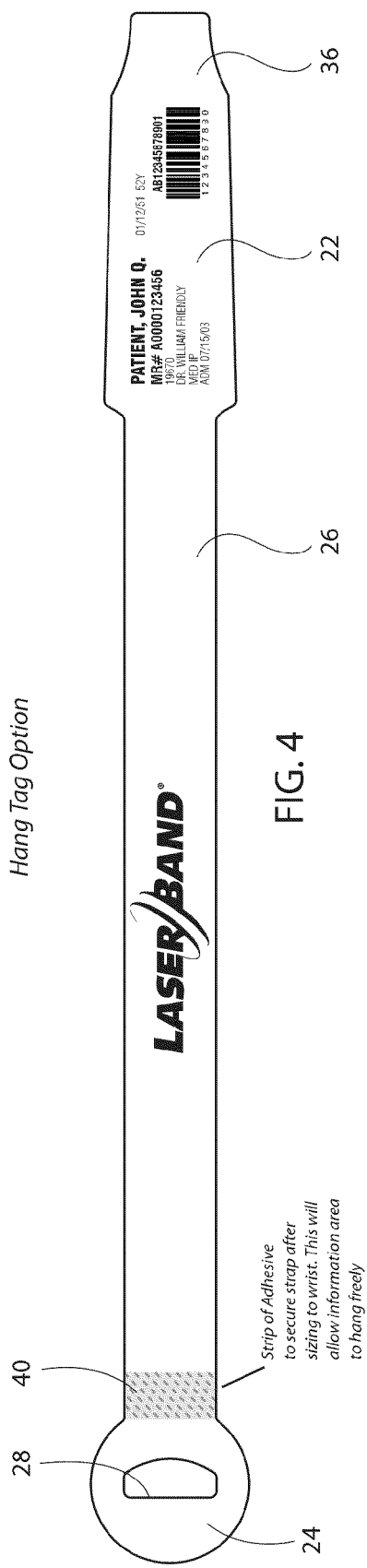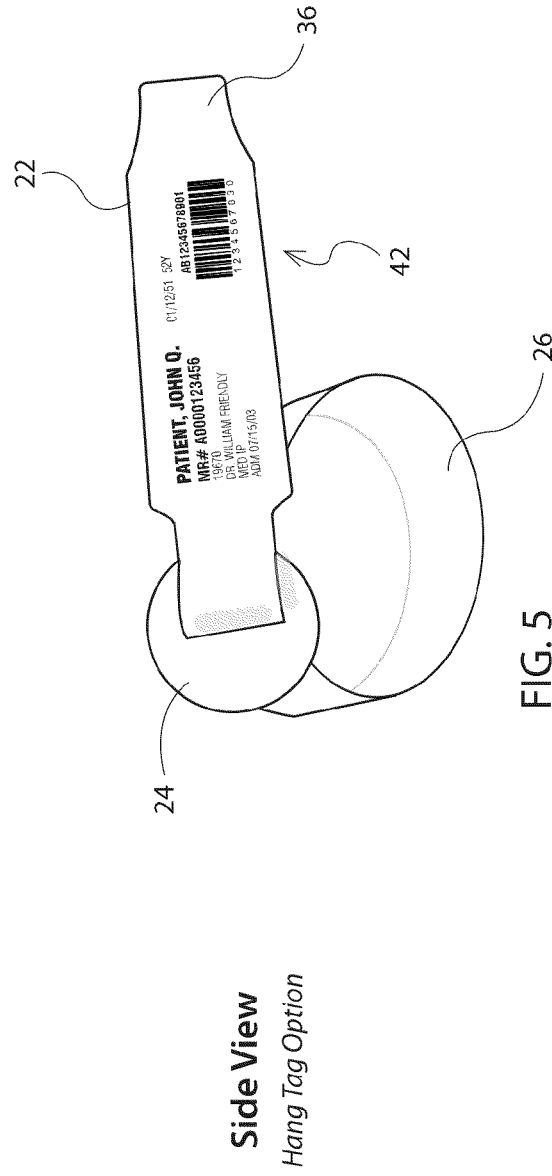
Top View
*Hang Tag Option*
FIG. 4
Side View
*Hang Tag Option*
FIG. 5

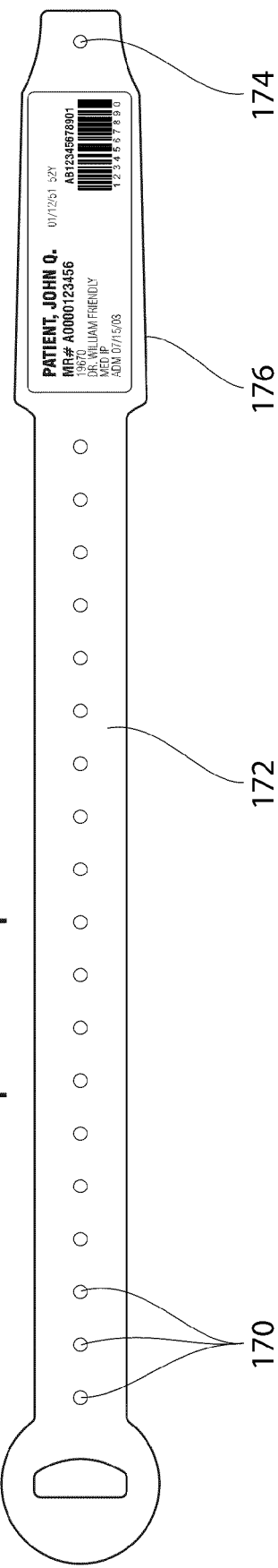
FIG. 15 (a) Snap Closure Option with Label
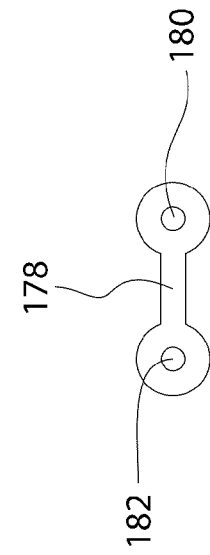
FIG. 15 (b)

WRISTBAND WITH SEPARATED IMAGING AREA AND CINCH SLOT

BACKGROUND AND SUMMARY OF THE INVENTION

Single use, inexpensive wristbands have been commercially available for many years and while early designs were principally plastic bands requiring separately printed labels, later designs improved on these both in cost and convenience by providing a self laminating wristband die cut into a page sized business form for processing through a laser printer. Other later designs also provided single layer or single ply wristbands similarly die cut into a carrier or page sized business form. These later designs are much less expensive, may be conveniently printed and assembled at the point of inpatient processing for health care applications, and are sufficiently sturdy to withstand the healthcare environment at least for temporary stays. The assignee of the present patent filing has experienced great success in this field and its products incorporating its wristband inventions and designs are market leaders not only in creativity, ingenuity, and inventiveness but also in commercial success. Just a few exemplary issued patents and published patent applications for these wristband inventions and designs include: U.S. Pat. Nos. 6,510,634; 7,386,949; 2007/0220796; 2007/0089342; 2008/0098636; 2008/0109937; and 2008/0250688; as well as unpublished patent application Ser. No. 12/026,030 filed Feb. 5, 2008; and Ser. No. 12/115,945, the disclosures of which are incorporated herein by reference.

A number of these wristband inventions and designs include a strap and cinch slot for attaching the wristband about a wearer's appendage, most often his wrist. Wristbands incorporating this unique attachment arrangement have met with great commercial success and are made and sold by the millions each year. Many of these designs incorporate the cinch slot at or in an imaging area, situated opposite an end of a strap often extending from the other side of the imaging area, so that the wristband is secured by looping the strap around the wrist and inserting it through the cinch slot before being doubled over and adhered back onto itself. Uniformly in these wristband designs/inventions the cinch slot and imaging area are consolidated at only one end of the wristband and the strap extends to an opposite end. In those instances when a "hang tag" is desired, a separate card with slot is provided and the wristband strap is inserted through the slot to "hang" it loosely from the wristband after it is attached to the wearer. As shown in one or more of the patents mentioned above, the separate card may itself be self-laminating, although it need not be depending on the desire of the purchaser and the intended application.

In its continuing efforts to design and develop new and inventive solutions to wristband needs, the inventors herein have designed and developed a new and novel wristband design which, in broad terms, comprises separating the cinch slot from the imaging area. By separating the imaging area from the cinch slot, and in at least one embodiment putting the imaging area at an opposite end of the strap from the cinch slot, a novel arrangement is achieved that has a number of advantages. For example, simply flexing or bending the imaging area permits it to be threaded through the cinch slot and then it naturally returns to its at rest configuration which provides an integrally formed mechanical fastening arrangement without further action by the nurse. And, when applied in this manner, a natural "hang tag" configuration is achieved without need of a separate slotted id card or the like. If provided with a patch of adhesive, and depending on where it is applied, the imaging area and wristband can be further secured in place either in hang tag mode or not in the event the outer edge of the imaging area has the adhesive. If the adhesive is applied to the outer edge, the imaging area is thus not only secured by an "interference fit" between its larger width against the narrower cinch slot, but also with adhesive at its opposite side. This arrangement allows the imaging area to be adhered or "locked down" to better conform to the wearer's wrist. The imaging area may be made to accept printing, such as by being processed through a laser printer, thermal printer or suitable other printer. Alternately, a separate label may be printed and adhered to the imaging area or a nurse may simply write information thereon.

To enhance the usability of the wristband, the imaging area may be shaped to not only make it easier to fit through the cinch slot but also increase the difficulty in removing it or backing it out through the cinch slot. One such shape is a taper, or "shovel", shape which has a narrower tip or outer end and a wider back end, to which an even more sharply tapered tip may be provided having a width narrower than the cinch slot so that it may be conveniently started into the cinch slot and assist in guiding the imaging area therethrough. The cinch slot itself may also be located in an enlarged cinch slot area or simply slot area, spaced from the imaging area and in one embodiment at least at an opposite end from the imaging area. In other embodiments, the imaging area may be provided with straps extending from either side and with the cinch slot area located at an outer end of one such strap with the other strap having either a continuous, uniform width smaller than the cinch slot or with a shovel formed at an outer end to provide the same interference fit closure. In an alternative, a second label may be applied to this second, outboard shovel and used for additional patient information or special precaution information such as Allergies, Fall Risk, or even Do Not Resuscitate.

The cinch slot may preferably be formed in an enlarged cinch slot area, or slot area, preferably located at an outboard end of a strap which has the imaging area preferably at the opposite end of the same strap. The cinch slot may be located otherwise, as desired by the user or to fit a particular application, but is preferably separated from the imaging area. The cinch slot may preferably have a shape facilitating the passing therethrough of the imaging area or shovel closure or strap end. One example of such a shape would be a "D" shape, which would preferably have a width greater than the strap, but narrower than the widest part of the imaging area or shovel, and an arcuate portion against which the imaging area or shovel could flex and be guided therethrough. A supplementary closure may be provided as desired, such as with a series of holes along a strap and a matching hole in the imaging area so that as the band is wrapped around a wearer's wrist, a joinder such as a clasp or male/female mating pin or the like may be fit through the aligned holes and join the strap to the imaging area or shovel.

The wristband invention as disclosed in its various embodiments may be constructed of a single ply of material, such a polyester or polyethylene film, or even a composite single ply of the same or similar materials. The material chosen may be suitable to allow for thermal printing of the wristband, die cut into a business form such as a carrier or page or sheetlet, and provided with self adhering labels or not. Another suitable material would be Tyvek® or the commercial equivalent. For thermal printing, the wristbands may be formed in separate carriers and then a plurality of carriers formed end to end in a roll. In an alternate embodiment, the wristbands may be formed of multiple plies of material, with one ply being a laminate for a self-laminating version, die cut into a business form in a fashion as exemplified in the patents mentioned above.

Several notable features of the wristband invention as contained in the several preferred embodiments include an imaging area that is shaped to pass through a cinch slot but yet provides a mechanical or interference fit or joinder for the wristband, a printer processible wristband with a non-adhesive but functional mechanical attachment, a wristband which automatically forms a hang tag upon being secured, a cinch slot separated from an imaging area unlike assignee's other wristband inventions incorporating a cinch slot, an imaging area which serves the dual purpose of receiving information desired to be displayed but also is shaped to form part of the wristband attachment, and more than one "shovel" or imaging area incorporated into a single wristband.

The foregoing explanation of several features of the several preferred embodiments of the invention has been given to be exemplary of the invention and not limiting. Additional features and a more detailed explanation is provided in connection with the drawings below.

BRIEF DESCRIPTION OF THE DRAWINGS

FIG. 2 is a bottom view of the wristband depicted in FIG. 1 with an adhesive patch at an end;

FIG. 3 is a perspective view of the assembled wristband depicted in FIGS. 1 & 2;

FIG. 4 is a top view of an alternative embodiment of the wristband of the present invention with an adhesive patch at an opposite end;

FIG. 5 is a perspective view of the assembled wristband depicted in FIG. 4;

FIGS. 15a & b depict an alternate embodiment of the wristband of the present invention having a series of holes along the strap and a snap closure.

DETAILED DESCRIPTION OF THE PREFERRED EMBODIMENTS

Figure 1:
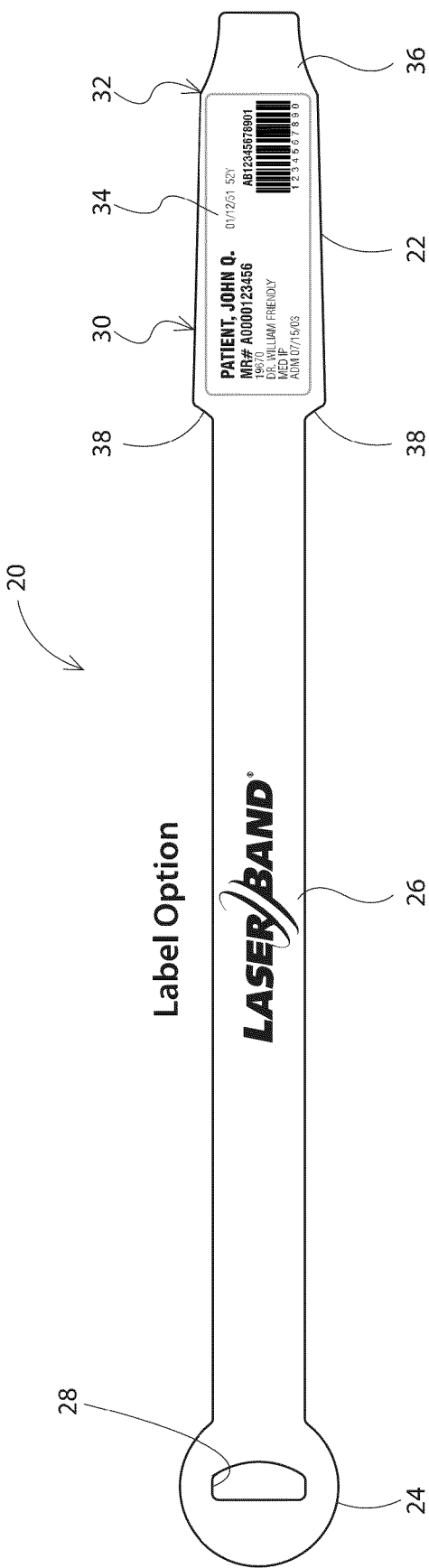
FIG. 1 is a top view of the wristband of the present invention having a separated imaging area and cinch slot.

The present wristband invention is shown and described for illustrative purposes only in the form of the several embodiments depicted in the drawings as explained in greater detail herein. However, the invention is to be considered as limited solely by the scope of the claims appended hereto.

As shown in FIG. 1, the wristband 20 of the present invention includes an imaging area 22 and an enlarged cinch slot area or simply enlarged slot area 24 joined by a strap 26. The imaging area 22 may be generally considered as shaped to interference fit through the cinch slot 28 formed in the enlarged slot area 24. By "interference fit", it is meant that the imaging area 22 has at least one dimension larger than the corresponding dimension of the cinch slot 28 an may be deflected, bent, folded, or otherwise deformed to pass through the cinch slot 28 and, preferably, return to a shape that inhibits its freely passing back through the cinch slot 28. In effect, the imaging area 22 may preferably act as a joinder for securing the wristband 20 about a wearer's appendage (referred to as a "wrist" herein for simplicity). While various shapes may be understood by one of skill in the art as capable of achieving this "interference fit", the inventors disclose as a preferred embodiment a shape that may be referred to as a "shovel" shape characterized by a back end 30 having a width larger than the cinch slot 28 tapering to a narrow end 32 forming an essential shape of a tapered rectangle and which is preferably sized to receive a self adhering label 34 with information printed thereon. Alternately, and as explained in further detail below, instead of a self adhering label 34, information may be hand written or printed directly onto the imaging area, or left blank, as desired. Further, preferably, a yet narrower nose 36 may extend from the leading, tapered end 32 and which preferably has a width narrower than the cinch slot 28 to help guide the imaging area 22 into the cinch slot 28 when it is desired to secure the wristband 20 to the wearer's wrist. The back end 30 may also have a shoulder 38 formed on either side which, after the imaging area 22 is passed through the cinch slot 28, "catches" on the enlarged slot area 24 to hinder the imaging area 22 from inadvertently passing back through which would inadvertently release the wristband from around the wrist. Other shapes and angles for this shoulder 38, and perhaps even only one shoulder 38, may be contemplated for effective use by one of skill in the art. The enlarged slot area 24 may preferably have a substantially circular shape, and in any event have a shape that will provide the necessary strength to hold the wristband in place when secured and avoid tearing. As shown, preferably, a "D" shaped cinch slot 28 is provided although other shapes may be readily understood by those skilled in the art as amenable to good use. The "D" shape does however provide a curvilinear edge which acts as a guide for deflecting the imaging area 22 into an arcuate shape to aid its being passed through for attachment. The strap 26, at whose ends the imaging area 22 and enlarged slot area 24 are formed, may be of a length suitable for the particular application. For example, a shorter length may be used for an infant's wrist while a longer strap would be more desirable for an adult. The width of the strap 26 is preferably less than the corresponding dimension of the cinch slot 28 so that the wristband may be sized to the particular wrist size merely by siding the strap further in or out of the cinch slot 28. In this embodiment, the wristband 20 is preferably formed of a single ply of material, such as Tyvek™ or other suitable material. The single ply of material may also comprise a composite ply of two or more materials, such as a 0.001" polyester film married to a 0.006" low density polyethylene film to form a soft by strong ply considered as preferable for application to a wristband for health care use. Other suitable materials could include films, fabrics, foams, etc. ranging in thickness from about 0.0005" up to about 0.125". The wristband 20 may be formed by die cuts in a business form, as depicted in other Figures and as described below.

As shown in FIGS. 2 & 3, the wristband 20 may also have a strip or patch of adhesive 40 applied at the nose 36 (or end of the imaging area 22) which may be used to adhere the nose 36 to the back of the strap 26 and further secure the wristband 20 in place about the wrist after the imaging area 22 has been passed through the cinch slot 28.

As shown in FIGS. 4 & 5, instead of applying the adhesive 40 to the nose 36, the adhesive may be applied at an end of the strap, or at the enlarged slot area 24, and used to adhere the strap and thereby not only size the wristband to a desired length but also create a hang tag 42. Thus, in this embodiment, an integrated hang tag wristband arrangement is formed for those applications where it is desired to have a hang tag for ready locating of the information applied to the hang tag.

Figure 6:
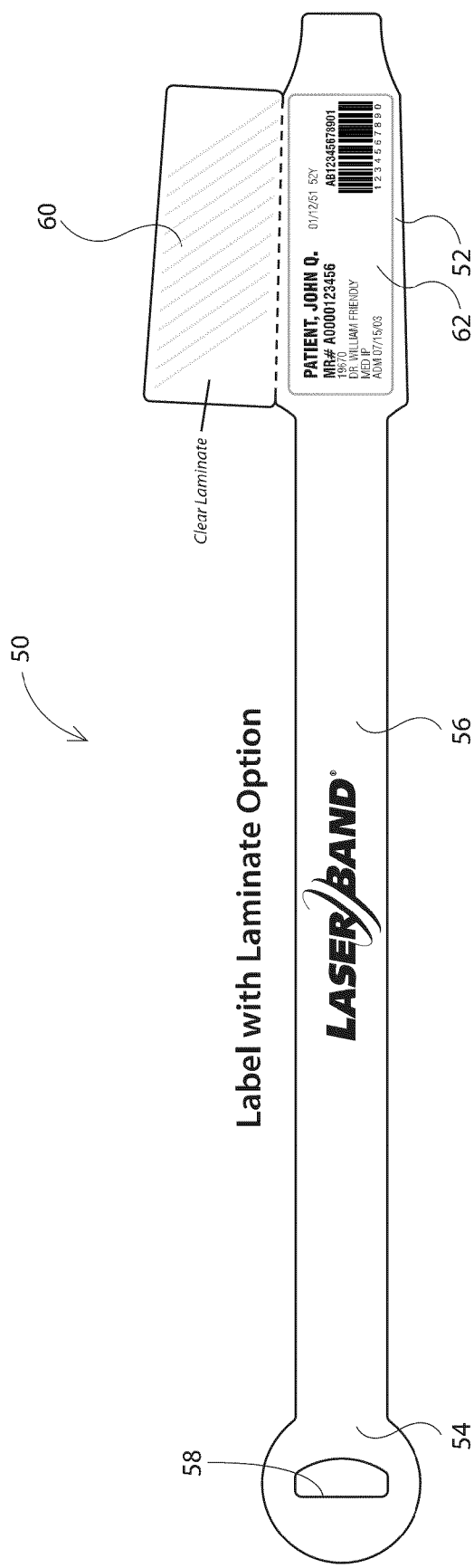
FIG. 6 is a top view of the wristband of the present invention having a self-laminating feature.

As shown in FIG. 6, a self-laminating wristband 50 may be constructed and have a first ply of material forming the imaging area 52, the enlarged slot area 54 and the strap 56. A cinch slot 58 is preferably formed in the enlarged slot area 54 as well. As an added extra, a laminate overlay, or laminating layer, 60 is provided so that the patient information is protected during use. The patient information may be directly applied to the imaging area 54, or a self adhering label 62 may contain the printed patient information. The laminate overlay 60 may be die cut into a second ply of material, a different ply than that from which the wristband 50 is die cut, and both separated from a business form or carrier as depicted in other drawing Figures and as described in other patents owned by the assignee hereof including those incorporated by reference above. Yet another alternative is that the laminating layer 60 may be "hinged" from the self adhering label 62 itself and is applied along with the label 62 to the imaging area 52.

Figure 7:
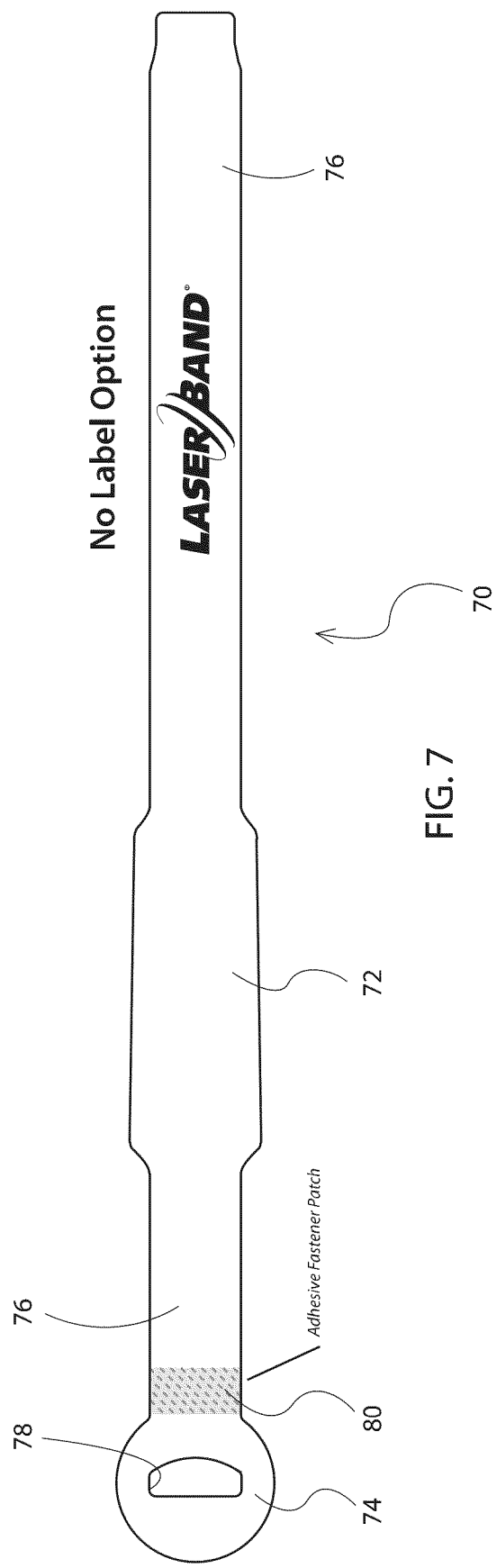
FIG. 7 is a top view of an alternate embodiment of the wristband of the present invention having a mediate imaging area and separated cinch slot/strap closure.
Figure 8:
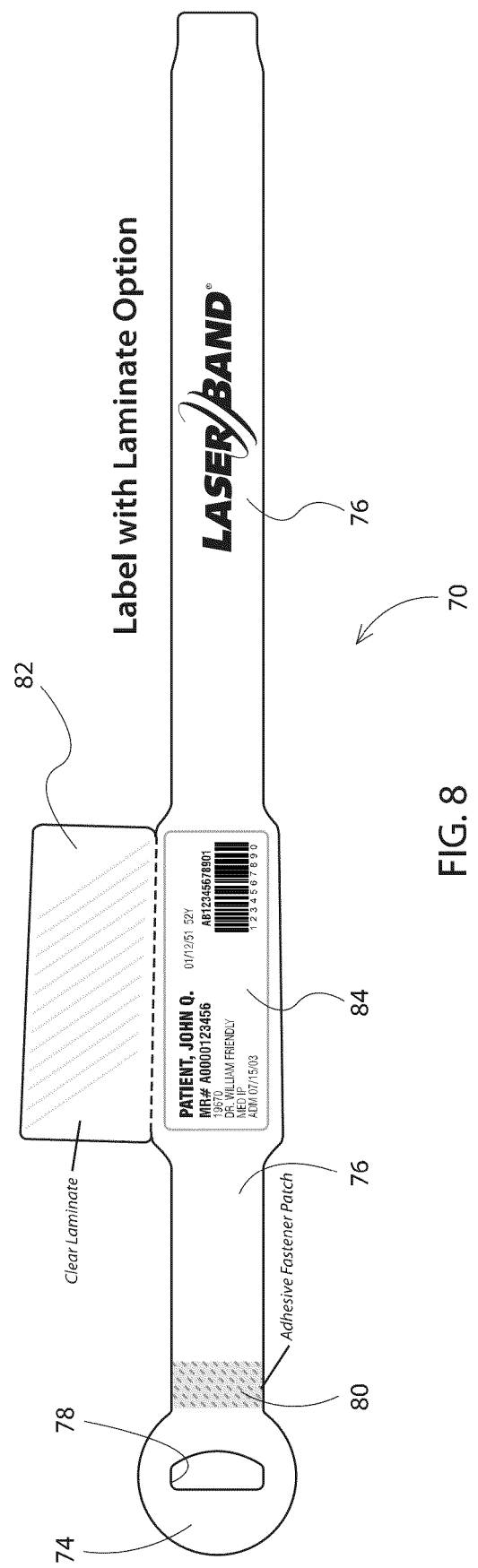
FIG. 8 is a top view of an alternate embodiment of the wristband depicted in FIG. 7 having a self-laminating mediate imaging area.

As shown in FIG. 7, a wristband 70 includes a centrally positioned imaging area 72, an enlarged slot area 74 and a pair of straps 76. In this embodiment the outer strap preferably fits freely through the cinch slot 78 and is adhered in place with adhesive applied as a patch or layer 80 at the enlarged slot area 74 or at the inner strap end. In this embodiment, the imaging area may preferably not receive any information. Furthermore, as the imaging area 72 is not interference fit through the cinch slot, the cinch slot may be provided in almost any shape, so long as it freely passes the outer strap therethrough. Alternately, a self adhering label, possibly pre-printed or printed with patient specific information, could also be applied, as desired. Depicted in FIG. 8 is a wristband 70 as shown in FIG. 7 except that a laminating layer 82 is provided to overlie and laminate a self adhering information bearing label 84 in a manner as previously described herein.

Figure 9:
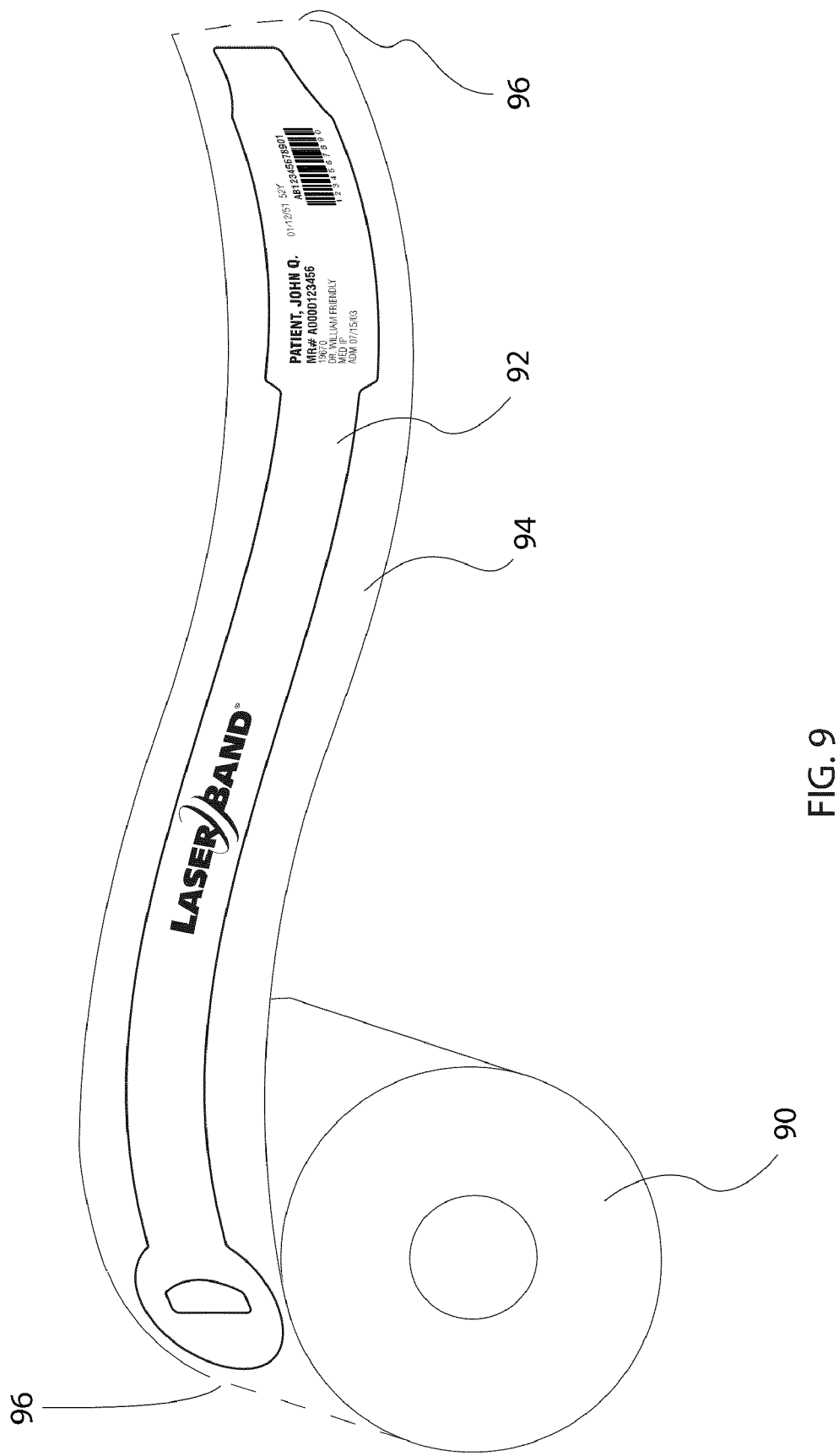
FIG. 9 is a perspective view of a roll of wristbands die cut into a continuous web.

As shown in FIG. 9, any one or more of the previously described wristband embodiments may be provided in a roll 90 comprised of a single common web into which each wristband is formed with a die cut 92 for convenient processing through a printer, such as a thermal printer. Alternately, each wristband may be formed by a die cut 90 in each of a plurality of carriers 94, with each carrier 94 being separable from the roll 90 by tearing along a leading and trailing perforation 96.

Figure 10:
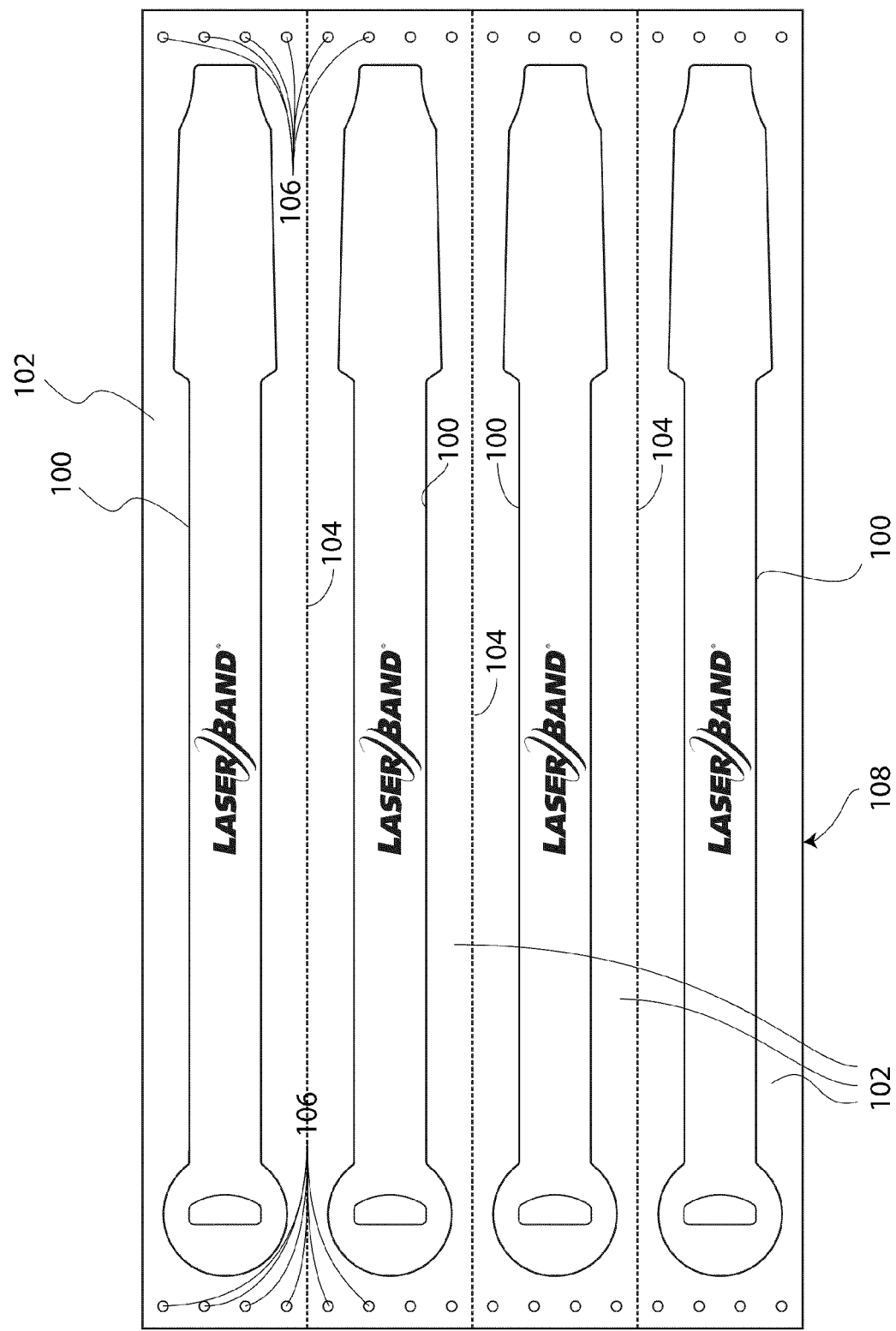
FIG. 10 is a top view of a business form having a plurality of wristbands formed in a plurality of individually separable carrier sheets.

As shown in FIG. 10, a series of wristbands comprised of any one or more of the various design wristbands disclosed and described herein may also be formed by a die cut 100 in carrier sheets 102, with the carrier sheets 102 being individually separable along a line of perforation 104 joining adjacent carrier sheets 102. To accommodate printers having tractor feed, a series of holes 106 may also be formed along each edge of the carrier sheets 102, as is known in the art. The plurality of carrier sheets 102 may be assembled into a page 108 of wristbands for printer processing through a sheet fed printer as well.

Figure 11:
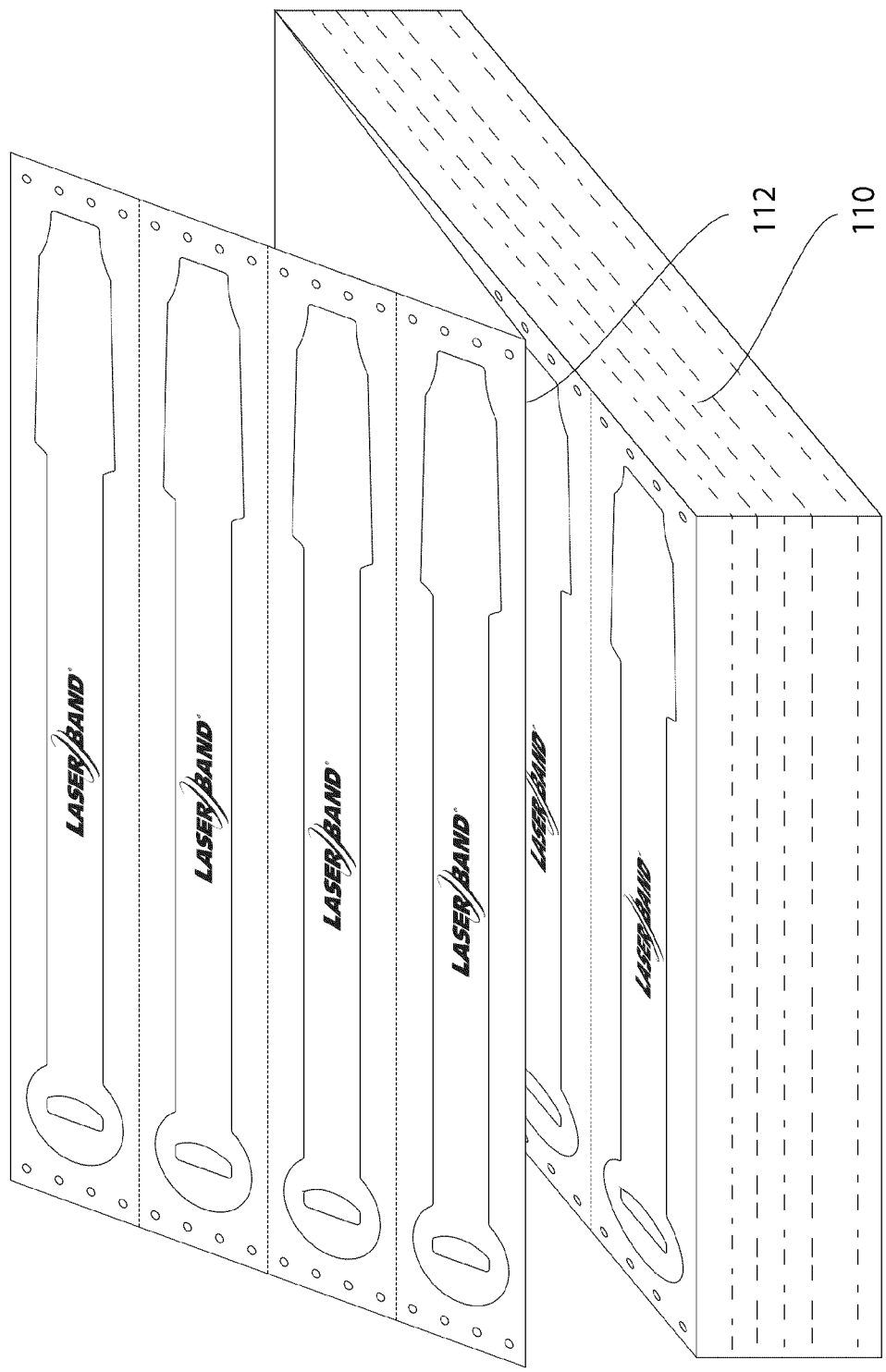
FIG. 11 is a perspective view of a plurality of business forms depicted in FIG. 10 assembled into a fan fold arrangement suitable for use with a tractor feed printer.

As shown in FIG. 11, a plurality of pages 108 may be assembled into a fan fold business form 110, with a line of perforation 112 joining adjacent pages, which is particularly suited for feeding through some printers, as is known in the art.

Figure 12:
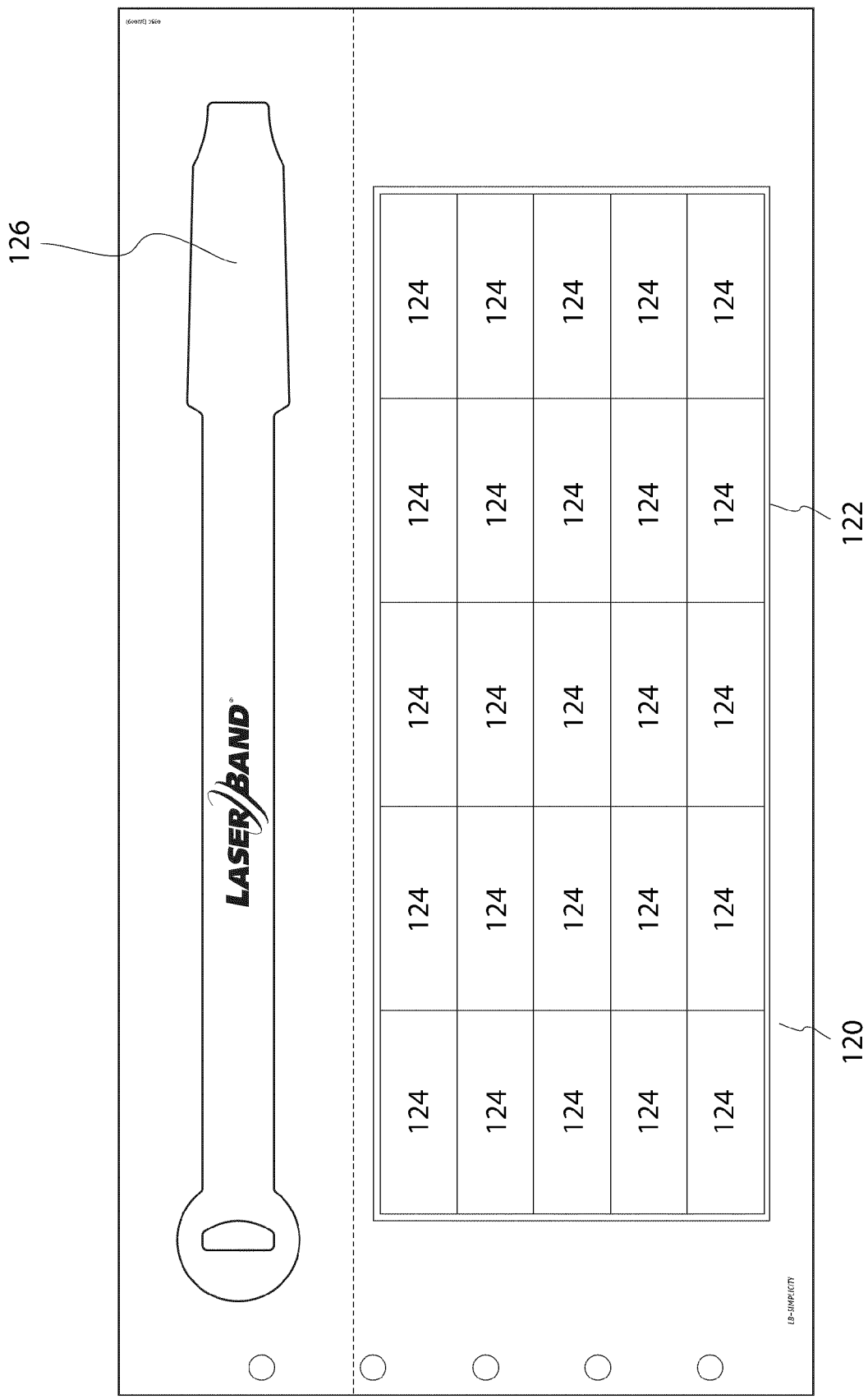
FIG. 12 is a top view of an alternate business form depicting the wristband of the present invention with a plurality of labels die cut therein.

As shown in FIG. 12, any one of the various wristband designs may be combined into a single sheet or page 120 with a matrix 122 of a plurality of labels 124, preferably self adhering. As shown, a 5×5 matrix 122 forming 25 labels 124 is conveniently fit onto a page 120 in a lower section with a single wristband 126 formed in the upper section of the page 120.

Figure 13:
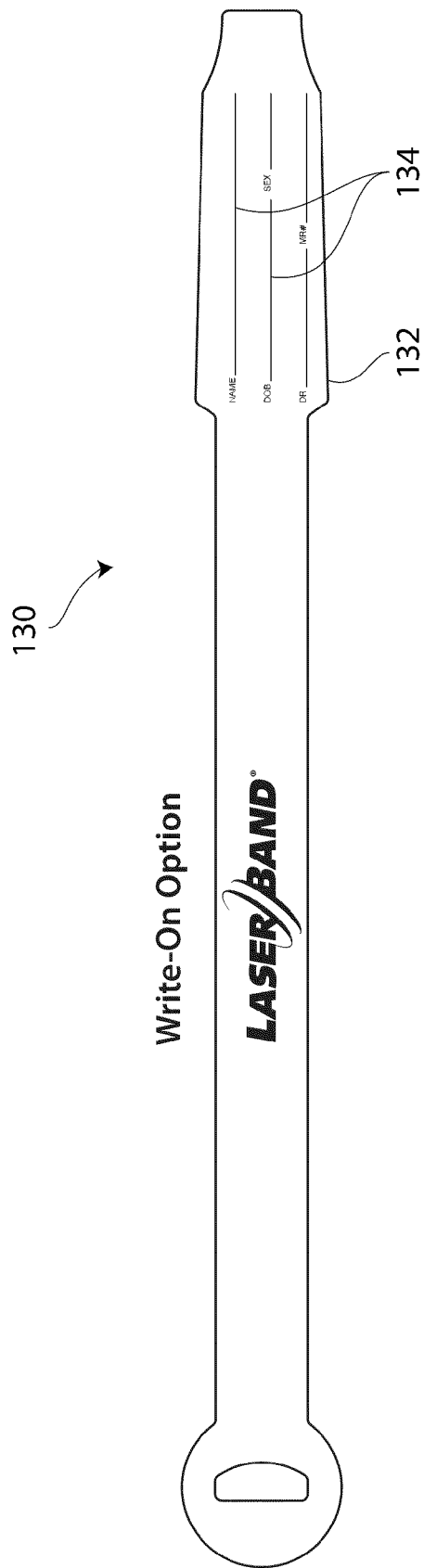
FIG. 13 is a top view of an alternate embodiment of the wristband of the present invention having a pre-printed imaging area to accept written information.

As shown in FIG. 13, a wristband 130 of any embodiment comprising an imaging area 132 may be pre-printed with a series of lines 134 to facilitate the hand writing of data or information directly onto the imaging area 132.

Figure 14:
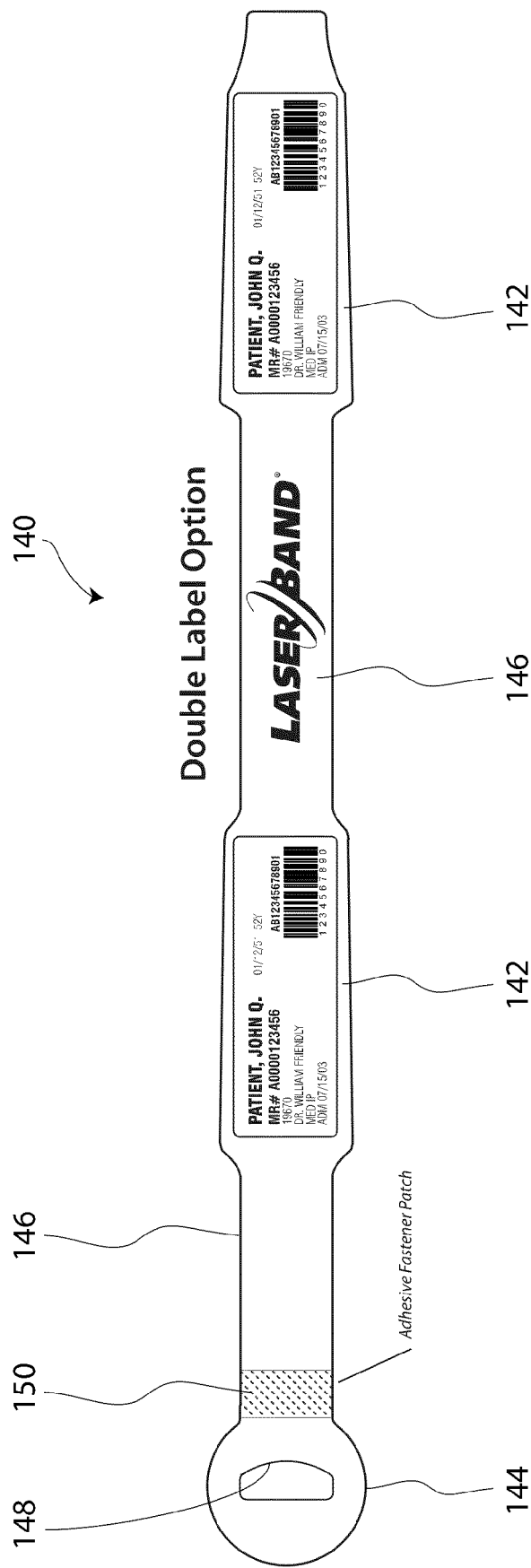
FIG. 14 is a top view of an alternate embodiment of the wristband of the present invention having two separated imaging areas.

As shown in FIG. 14, a wristband 140 may be provided with two imaging areas 142, separated by a strap 144 instead of a single imaging area. Although these imaging areas 142 are depicted as being of approximately the same size, the imaging area nearest the enlarged slot area 144 may be longer and possibly extend all the way to the enlarged slot area 144, it being preferable that at least a short section of strap 146 be provided adjacent the outer imaging area 142. This one length of strap, which is preferably sized to freely slide through the cinch slot 148, allows the band to be sized appropriately and also permits the imaging area to act as a joinder in combination with the cinch slot 148. A double imaging area wristband permits one to be used to display the usual patient information while the other could be used as a "special precautions" identifier, such as "allergy alert" or "fall risk" or even "do not resuscitate". An adhesive patch or layer 150 may be provide to permit the outside imaging area to be sealed down, or if desired, the outside imaging area may be left free to thereby act as a hang tag.

As shown in FIGS. 15a & b, an alternate wristband design may include a series of holes 170 formed along the length of the strap 172, and a mating hole 174 formed in the imaging area 176 (or strap end depending on the wristband design being considered). The wristband may then be further affixed in place by snapping together the snap closure 176 having a male post 178 which snaps into a female hole 180 when aligned with hole 174 and one of holes 170. This arrangement may be used in place of a layer or patch of adhesive to clamp down the outer edge of the imaging area 176.

Figure 16:
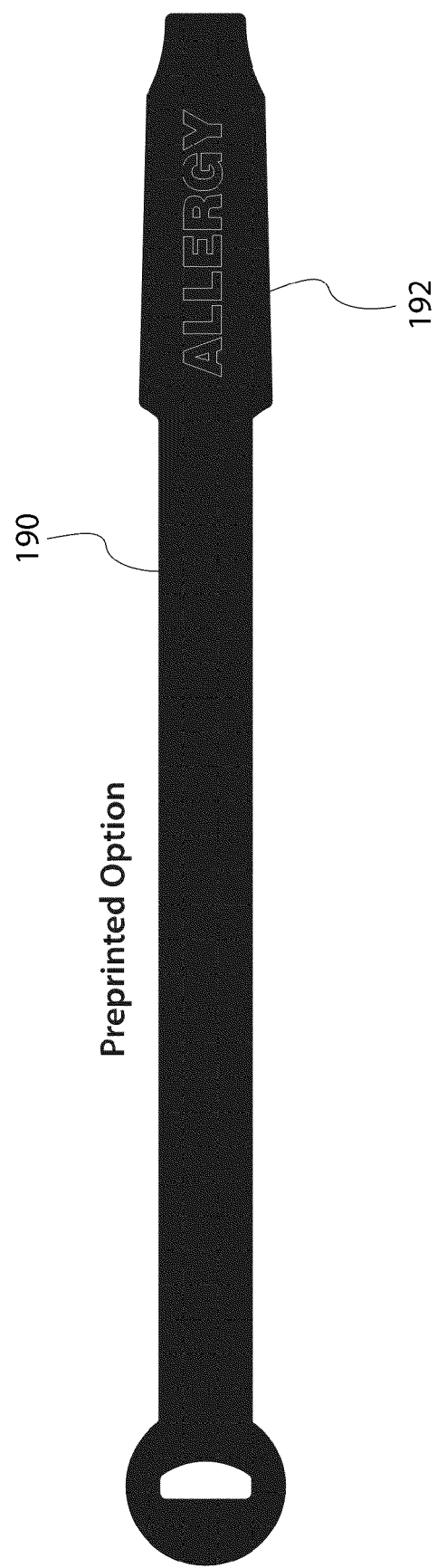
FIG. 16 is a top view of another embodiment of the wristband of the present invention pre-printed for special precautions.

As shown in FIG. 16, a preprinted wristband design 190 may be colored a representative color, such as orange, and then preprinted with a special precautions indication, such as "Allergy" as shown in the drawing. The imaging area may then be used as a joinder, as previously described, to attach the wristband 190 to a patient.

Although for convenience only a single design wristband has been shown in the various business forms depicted herein, it would be understood by those of skill in the art that any of the wristband embodiments disclosed herein may be included in a business form as shown in FIG. 9-12.

The present invention has been depicted in the drawings and described in the specification in several embodiments all of which are intended to comprise examples of the invention and for illustrative purposes and not in any sense to limit the invention. Those of skill in the art would recognize and understand that various changes could be readily made to these specific embodiments and yet remain within the teaching and scope of the present invention, which should be limited solely to the scope of the claims and their equivalents.

What is claimed is:

1. A wristband having an imaging area and a cinch slot situated with a strap extending therebetween, said imaging area being shaped to facilitate its fitting through said cinch slot, a narrower end of said shaped imaging area being at an end of said wristband and sized larger than but capable of being fit through the cinch slot and a patch of adhesive applied at the imaging area to thereby secure the wristband about a wearer's appendage.

2. The wristband of claim 1 wherein said wristband comprises a single ply of material and wherein said imaging area has a width greater than the cinch slot width so that after being fitted therethrough the imaging area is retained.

3. The wristband of claim 2, further comprising an information bearing label adhered to said imaging area.

4. The wristband of claim 1 wherein said narrower end comprises a nose having a reduced width to facilitate insertion thereof into said cinch slot, said patch of adhesive being applied to said nose.

5. The wristband of claim 1 wherein said imaging area is sized to interference fit through said cinch slot.

6. The wristband of claim 5 wherein said cinch slot and imaging area are at opposite ends of said wristband.

7. The wristband of claim 6 wherein said strap is sized to freely move through the cinch slot.

8. The wristband of claim 7 wherein said cinch slot opening is substantially "D" shaped.

9. The wristband of claim 6 wherein said cinch slot comprises an opening having at least one curvilinear edge.

10. The wristband of claim 1 further comprising a slot area formed at an end of said strap, said cinch slot being located in said slot area.

11. The wristband of claim 10 wherein said slot area has a width greater than the width of said strap.

12. The wristband of claim 1 wherein said imaging area is tapered and has a width sufficient so that a portion thereof overlaps either side of a standard sized label adhered thereto.

13. The wristband of claim 1 further comprising a laminating layer for overlying the imaging area.

14. A printer processible business form comprising a layer of single ply material having a die cut defining the wristband of claim 1 therein.

15. The business form of claim 14 wherein said business form comprises a page.

16. The business form of claim 15 further comprising a plurality of self adhering labels die cut in said business form.

17. A wristband having an imaging area and a cinch slot situated with a strap extending therebetween, said imaging area being sized larger than but capable of being fit through the cinch slot to thereby secure the wristband about a wearer's appendage, a layer of adhesive applied to a portion of said wristband for adhering the imaging area after it is fitted through the cinch slot to thereby help secure the wristband in place on a wearer's appendage, and a protective covering for said adhesive layer to prevent its exposure until its desired use.

18. The wristband of claim 17 wherein said layer of adhesive is applied to the strap.

19. The wristband of claim 17 wherein said layer of adhesive is applied to the imaging area.

20. A single ply wristband having an imaging area at one end, an enlarged slot area at its other end, a cinch slot formed in said enlarged slot area, a strap extending between said imaging area and said enlarged slot area, said strap having a width smaller than the width of the cinch slot and the imaging area having a width larger than the width of the cinch slot, a layer of adhesive applied to at least a portion of said wristband to help secure the wristband in place upon a wearer's appendage, and a protective covering for said layer of adhesive to prevent its exposure until desired to be used.

21. A printer processible business form comprising a layer of single ply material having a die cut defining the wristband of claim 20 therein.

22. The business form of claim 21 wherein said business form comprises a continuous strip of a plurality of individually separable carriers, each of which has at least one wristband die cut therein.

23. The business form of claim 21 wherein said business form comprises a page.

24. The wristband of claim 20 wherein said single ply is a composite ply made of a plurality of materials.

25. The wristband of claim 20 wherein said single ply is comprised of a plastic film.

26. The wristband of claim 20 wherein said cinch slot comprises an opening having a shape through which the imaging area may be fit through upon being flexed, said imaging area having at least one shoulder at an inboard edge thereof to resist unintended withdrawal of the imaging area through the cinch slot.

27. A printer processible business form having a die cut therein defining a single ply wristband having an imaging area and a separated enlarged slot area, a cinch slot formed in said enlarged slot area, a strap extending between said imaging area and said enlarged slot area, the imaging area having a size restricting its free movement through the cinch slot, and a layer of adhesive applied to at least a portion of said wristband to help secure the wristband in place upon a wearer's appendage.

28. The business form of claim 27 wherein said business form comprises a page and further comprising a plurality of detachable labels die cut therein.

29. A wristband having an imaging area and a separated slot area joined by a strap therebetween, said separated slot area having a cinch slot formed therein for securing the wristband about a wearer's appendage, a second strap extending from a side of said imaging area opposite the slot area, the second strap being sized to interference fit through said cinch slot and a patch of adhesive applied to an end of the second strap to thereby secure the wristband.

30. The wristband of claim 29 further comprising a label adhered to said imaging area.

31. The wristband of claim 29 wherein said second strap is sized to slide freely through the cinch slot.

32. The wristband of claim 31 wherein said imaging area has a taper to facilitate its insertion through the cinch slot.

33. A printer processible business form comprised of a single ply of material having a die cut defining the wristband of claim 29.

34. A printer processible business form comprised of a single layer of material and having a die cut therein forming the wristband of claim 29.

35. The business form of claim 34 further comprising a second layer of material having a die cut therein defining a laminating flap for laminating the imaging area.

36. A wristband comprising a joinder including an imaging area near one end thereof, a cinch slot wherein said wristband is applied to a wearer's appendage at least in part by inserting the joinder through the cinch slot to interference fit therewith, and a patch of adhesive applied to an end of the wristband to help secure it in place about a wearer's appendage.

37. The wristband of claim 36 wherein said cinch slot is formed in an enlarged slot area and further comprising at least one strap, said at least one strap connecting the imaging area to the enlarged slot area.

38. The wristband of claim 36 further comprising an imaging area connected between the joinder and the cinch slot with a pair of straps.

39. The wristband of claim 38 wherein said joinder is tapered.

40. The wristband of claim 38 further comprising a layer of adhesive applied at an end of the joinder.

41. A printer processible business form comprised of a single ply and having a die cut forming the wristband of claim 36.

42. An integrated wristband and hang tag comprising a hang tag including an imaging area at one end of said wristband, an enlarged slot area at an opposite end of said wristband, said enlarged slot area having a cinch slot therein, a strap extending between said hang tag and said enlarged slot area with said hang tag being sized to interference fit through the cinch slot, and a patch of adhesive applied to the wristband to secure said wristband to a wearer's appendage.

43. The integrated wristband of claim 42 wherein said hang tag comprises an imaging area for receiving printed information.

44. The integrated wristband of claim 43 further comprising a plurality of holes extending along the length of the strap and a hole at an end of the imaging area so that as said wristband is wrapped around a wearer's wrist the imaging area hole may be brought into alignment with one of said strap holes for fitting therethrough of a clasp.

* * * * *